(12) United States Patent
Liu et al.

(10) Patent No.: US 9,499,490 B2
(45) Date of Patent: Nov. 22, 2016

(54) FLUOROPHENYL PYRAZOL COMPOUNDS

(71) Applicant: Eli Lilly and Company, Indianapolis, IN (US)

(72) Inventors: Kevin Kun-Chin Liu, Shanghai (CN); Yinong Xie, Shanghai (CN); Liang Wu, Shanghai (CN); Guoqiang Zhou, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/037,344

(22) PCT Filed: Dec. 11, 2014

(86) PCT No.: PCT/US2014/069785
§ 371 (c)(1),
(2) Date: May 18, 2016

(87) PCT Pub. No.: WO2015/094913
PCT Pub. Date: Jun. 25, 2015

(65) Prior Publication Data
US 2016/0289195 A1    Oct. 6, 2016

(30) Foreign Application Priority Data

Dec. 19, 2013  (WO) ................ PCT/CN2013/089987

(51) Int. Cl.
| | |
|---|---|
| A61K 31/415 | (2006.01) |
| C07D 231/18 | (2006.01) |
| A61K 31/4439 | (2006.01) |
| C07D 401/12 | (2006.01) |

(52) U.S. Cl.
CPC .......... C07D 231/18 (2013.01); A61K 31/415 (2013.01); A61K 31/4439 (2013.01); C07D 401/12 (2013.01)

(58) Field of Classification Search
CPC .......... A61K 31/415; A61K 31/4439; C07D 231/18; C07D 401/12
USPC ............. 514/341, 407; 546/275.4; 548/366.1
See application file for complete search history.

(56) References Cited

U.S. PATENT DOCUMENTS 7,253,204 B2    8/2007  Delorme et al.
2016/0096823 A1    4/2016  McMillen et al.

FOREIGN PATENT DOCUMENTS

| WO | 01/24796 | 4/2001 | |
|---|---|---|---|
| WO | 02/00651 | 1/2002 | |
| WO | 02/078699 | 10/2002 | |
| WO | WO 02078699 A1 * | 10/2002 | ............ A61K 31/00 |
| WO | 03/031434 | 4/2003 | |
| WO | 03/051906 | 6/2003 | |
| WO | 2010/065879 | 6/2010 | |
| WO | 2012/030922 | 3/2012 | |

* cited by examiner

Primary Examiner — Kamal Saeed
Assistant Examiner — Janet L Coppins
(74) Attorney, Agent, or Firm — Macharri R. Vorndran-Jones

(57) ABSTRACT

The present invention provides a compound of the Formula: wherein X is selected from the group consisting of, R is selected from the group consisting of H and $CH_3$; R1 is selected from the group consisting of H, $CH_3$, F, Cl, $OCH_3$, C(O)OH, $C(O)NH_2$ or a pharmaceutically acceptable salt thereof.

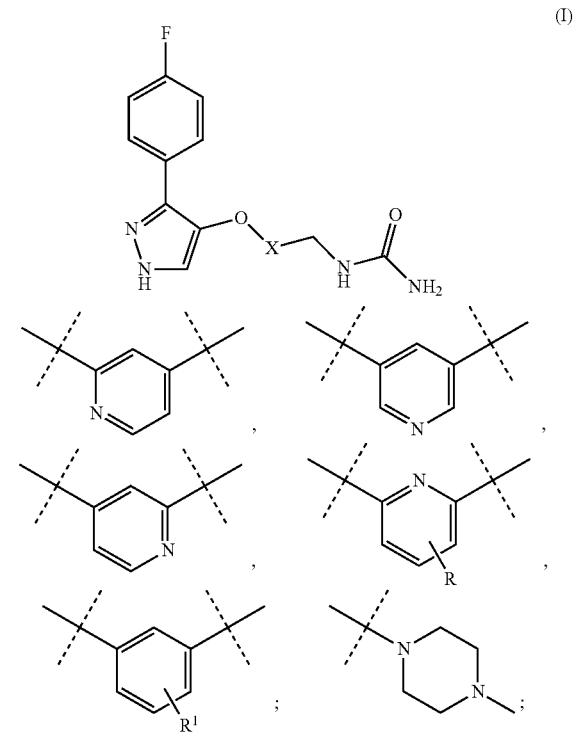

13 Claims, No Drawings

FLUOROPHENYL PYRAZOL COMPOUNDS

This invention relates to compounds or pharmaceutically acceptable salts thereof, and therapeutic use thereof. Compounds of this invention are inhibitors of methionine aminopeptidase 2 (MetAP2).

Obesity is a complex medical disorder resulting in excessive accumulation of adipose tissue mass. Today obesity is a world-wide public health concern that is associated with cardiovascular disease, diabetes, certain cancers, osteoarthritis, and other undesired health outcomes. The treatment of obesity strives to reduce excess body weight, improve obesity-related morbidity, and maintain long-term weight reduction. Approved drugs for treating obesity offer particularly unsatisfactory efficacy for severely obese subjects. There is a need for alternative treatment options to induce desired weight loss in a patient.

Increased expression of the MetAP-2 gene has been historically associated with various forms of cancer; however, WO 2010/065879 reports molecules inhibiting the enzymatic activity of MetAP-2 for use in treating obesity. There is a need for novel inhibitors of MetAP-2 for use in treating a condition associated with MetAP-2 increased expression.

The present invention provides novel compounds which are MetAP2 inhibitors. MetAP2 inhibitor compounds are desired to provide treatments for MetAP2 mediated conditions, such as obesity.

The present invention provides a compound of the Formula I below:

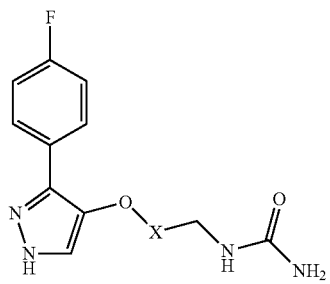

I wherein X is selected from the group consisting of

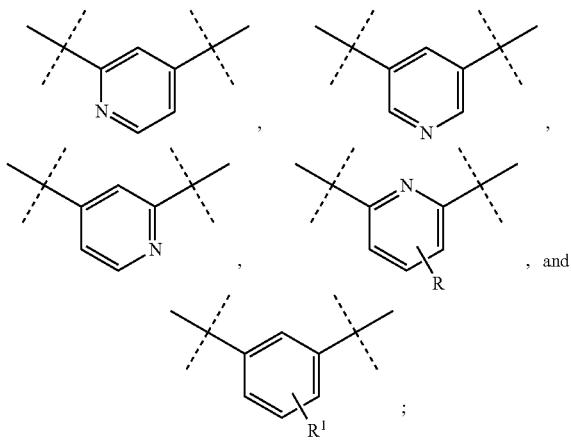

R is selected from the group consisting of H and CH₃;
R¹ is selected from the group consisting of H, CH₃, F, Cl, OCH₃, C(O)OH, C(O)NH₂ and

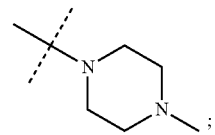

;

or a pharmaceutically acceptable salt thereof.

In an embodiment of the invention, X is selected from the group consisting of

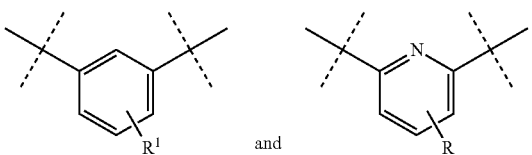

In an embodiment of the invention X is

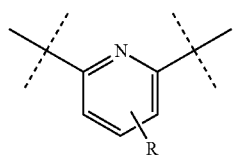

In another embodiment of the invention, X is

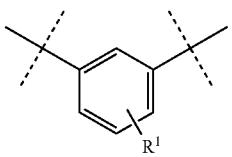

In an embodiment of the invention R¹ is selected from the group consisting of H, F, and CH₃. In an embodiment R¹ is

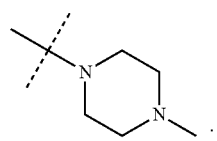

.

In an embodiment of the invention R is CH₃.

In a preferred embodiment, the compound is [3-[[3-(4-Fluorophenyl)-1H-pyrazol-4-yl]oxy]phenyl]methylurea, or a pharmaceutically acceptable salt thereof. In a preferred embodiment the compound is [6-[[3-(4-Fluorophenyl)-1H-pyrazol-4-yl]oxy]-5-methyl-2-pyridyl]methylurea or a pharmaceutically acceptable salt thereof.

The present invention also provides a pharmaceutical composition comprising a compound of Formula I as described above or a pharmaceutically acceptable salt thereof together with one or more pharmaceutically acceptable carriers, diluents or excipients.

The present invention also provides a method for treating obesity in a mammal. The method comprises administering to the mammal in need of treatment a compound as described above for Formula I, or a pharmaceutically acceptable salt thereof. The invention provides a method for inducing desired weight loss in a mammal in need thereof, comprising administering an effective amount of a compound of Formula I. The invention provides a method for therapeutic weight weight loss in a mammal in need thereof, comprising administering an effective amount of a compound of Formula I.

The present invention provides a compound according to Formula I or a pharmaceutically acceptable salt thereof as described above for use in therapy.

In yet another form, the present invention provides a compound as described above according to Formula I, a pharmaceutically acceptable salt thereof, or pharmaceutical composition for use in the treatment of obesity in a mammal in need thereof. Preferably the mammal is a human.

The present invention provides use of a compound according to Formula I, or a pharmaceutically acceptable salt thereof, in the manufacture of a medicament for the treatment of obesity. The present invention provides the use of a compound according to Formula I, or a pharmaceutically acceptable salt thereof, for use in the manufacture of a medicament for use in providing therapeutic weight loss.

Compounds of the present invention can be provided as a pharmaceutically acceptable salt. "Pharmaceutically-acceptable salt" refers to salts of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The abbreviations used herein are defined according to *Aldrichimica Acta*, Vol. 17, No. 1, 1984. Other abbreviations are defined as follows: "BSA" refers to Bovine Serum Albumin; "DMF" refers to N,N-dimethylformamide; "DIO" refers to diet induced obese; "HEC" refers to hydroxy ethyl cellulose; "HEPES" refers to 4-(2-hydroxyethyl)-1-piperazineethanesulfonic acid; "HWD" refers to high fat diet; "$IC_{50}$" refers to the concentration of an agent that produces 50% of the maximal inhibitory response possible for that agent; and "THF" refers to tetrahydrofuran.

The intermediates described in the following Schemes and preparations may contain a number of nitrogen, hydroxy, and acid protecting groups such as esters. The variable protecting group may be the same or different in each occurrence depending on the particular reaction conditions and the particular transformations to be performed. The protection and deprotection conditions are well known to the skilled artisan and are described in the literature. See. e.g., Greene and Wuts, *Protective Groups in Organic Synthesis*, (T. Greene and P. Wuts, eds., 2d ed. 1991).

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

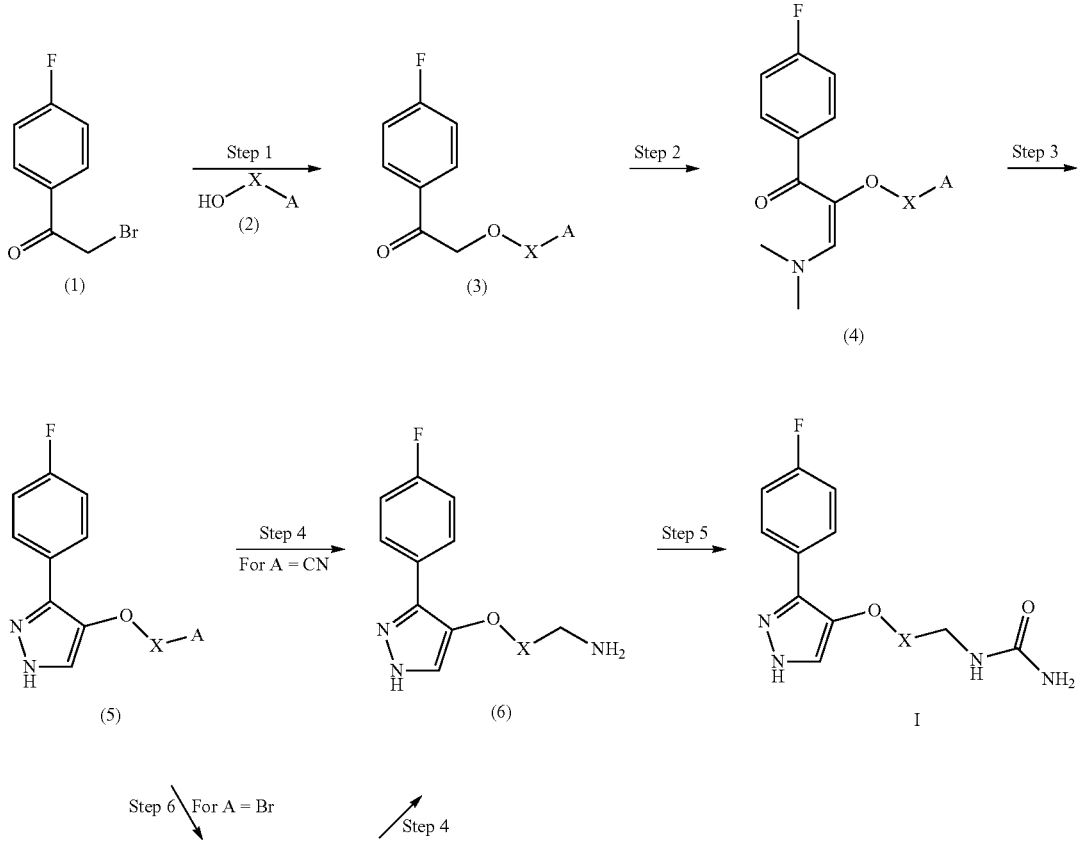

(7)

A = CN or Br

A compound of Formula I can be prepared in accordance with reactions as depicted in Scheme 1. Scheme 1 (Step 1) depicts the alkylation of a 2-bromo-1-(4-fluorophenyl)ethanone (1) with a substituted aryl or pyridyl hydroxy nitrile (2) as denoted by X with X defined previously. The bromo (1) reagent is reacted with the aryl or heteroaryl hydroxy compound (2) under basic conditions well known in the art using an inorganic base such as potassium carbonate in a polar aprotic solvent such as acetonitrile or acetone at room temperature or refluxing conditions to give compound 3, Step 1. Compound 3 is alkylated with N,N-dimethylformamide dimethyl acetal in a non-polar solvent such as toluene under refluxing conditions or microwave irradiation to give compound 4, Step 2, the substituted dimethylamino prop-2-ene-1-one compound (4). Compound 4 can be isolated or carried on in-situ to Step 3 to form the pyrazole compound (5). The pyrazole can be formed with hydrazine hydrate in a non-polar solvent such as toluene under microwave irradiation or alternatively with hydrazine hydrochloride using an organic base such as triethylamine in a polar protic solvent such as ethanol at refluxing conditions to give the substituted cyclized pyrazole (5). For A=nitrile, the nitrile on the pyridyl or phenyl (5) can be reduced to the amine (6) using reducing conditions well known in the art such as lithium aluminum hydride in a polar aprotic solvent such as THF or under hydrogen conditions using Raney nickel in a methanol ammonia solution to give the amine (6, Step 4). The methyl urea compounds of Formula I can be formed from the amine (6) using phenylurethane in a polar aprotic solvent such as THF and an organic base such as diisopropylethylamine while heating to about 80° C. under microwave irradiation conditions to give compounds of Formula I (Step 5). Alternatively, an inorganic base such as potassium cyanide and an acid such as acetic acid in a polar protic solvent such as methanol with heating to about 80° C. under microwave irradiation conditions can be used to convert the amine (6) to the methyl urea compounds of Formula I (Step 5). For A=Br, the bromide can be converted to the nitrile (7, Step 6) under palladium conditions well known in the art using ZnCN and a palladium(0) catalyst such as [1,1'-bis (diphenylphosphino) ferrocene]dichloropalladium(II) with zinc and zinc acetate in dimethylacetamide with heating to about 160° C. to give the nitrile compound (7, Step 6) which can be carried on to compounds of Formula I as described above for Steps 4 and 5. Alternatively, the nitrile (7) can be formed using copper cyanide and a base such as N-methyl pyrrolidine and heating to about 200° C. followed by the addition of ethylene diamine to give compound (7, Step 6).

Scheme 2

Alternatively, in Scheme 2, for A=Br of compound 2, the bromide (2) can be converted to a nitrile using copper cyanide in a polar solvent such as N-methylpyrrolidone and heated to about 200° C. under microwave irradiation to give a nitrile. (8). This hydroxy nitrile can then be reacted with compound (1) in Scheme 1, Step 1, as described in Scheme 1 and carried on to give compounds of Formula I as described above for Scheme 1, Steps 2-5.

The following preparations and examples further illustrate the invention and represent typical synthesis of the compound of Formula (I). Unless noted to the contrary, the compounds illustrated herein are named and numbered using Accelrys Draw 4.0, IUPACNAME ACDLABS or Symyx/Draw 4.0.

Preparation 1

4-Fluoro-3-hydroxy-benzonitrile

Add lithium chloride (1.7 g, 40 mmol) to a stirred solution of 4-fluoro-3-methoxybenzonitrile (2.0 g, 13 mmol) in DMF (26 mL). Stir the resulting mixture at 160° C. for 5 hours and then cool to room temperature with stirring for 12 hours. Dilute the mixture with ethyl acetate (50 mL) and wash with water (2×40 mL). Acidify the isolated aqueous phase with 1 M HCl and extract with ethyl acetate (3×60 mL). Wash the combined organic extracts with water (2×100 mL), dry over Na₂SO₄, and concentrate under reduced pressure to give the title compound as a yellow solid (0.68 g, 38%): ES/MS (m/z) 138 (M+H), which is directly used without further purification.

Preparation 2

5-Hydroxy-2-methyl-benzonitrile

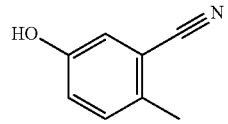

Add a solution of sodium nitrile (2.1 g, 31 mmol) in water (15 mL) drop wise at 5° C. to a stirred solution of 5-amino-2-methylbenzonitrile (4.0 g, 31 mmol) in 33% sulfuric acid (45 mL) and keep the temperature below 5° C. In a separate flask, add concentrated sulfuric acid (30 mL) cautiously to a stirred solution of sodium sulfate (21.7 g, 153 mmol) in water (15 mL) and heat the mixture to reflux. Add the prepared diazonium solution to the refluxing mixture in portions and continue refluxing for 2 hours. Cool the mixture slowly to room temperature and stir overnight. Extract the mixture with ethyl acetate (2×100 mL) and wash the combined organic extracts with water (2×150 mL) and 10% NaOH water solution (3×100 mL). Acidify the combined NaOH extracts with concentrated HCl and then extract with ethyl acetate (2×200 mL). Dry the organic extracts over $Na_2SO_4$ and concentrate under reduced pressure to give the title compound as a yellow solid (2.4 g, 60%): ES/MS (m/z) 134 (M+H), which is used directly without further purification.

Preparation 3

3-Cyano-5-hydroxy-benzoic acid

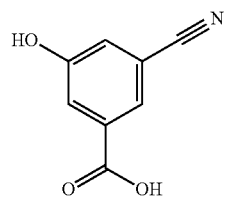 [SMILES: N#Cc1cc(O)cc(C(=O)O)c1]

Add copper cyanide (0.90 g, 10 mmol) to a stirred solution of 3-bromo-5-hydroxybenzoic acid (2.2 g, 10 mmol) in N-methylpyrrolidone (12 mL). Heat the mixture to 200° C. under microwave irradiation for 2 hours. Pour the mixture into 1 M HCl water solution (100 mL) and extract with ethyl acetate (3×50 mL). Combine the organic extracts, wash with brine, dry over $Na_2SO_4$ and concentrate under reduced pressure to give the title compound as a brown solid (1.5 g, 92%). ES/MS (m/z) 164 (M+H), which is used directly without further purification.

Preparation 4

Methyl 3-cyano-5-hydroxy-benzoate

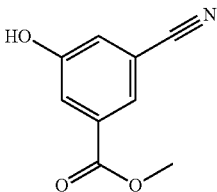

Add concentrated sulfuric acid (0.42 mL, 7.9 mmol) into a stirred solution of 3-cyano-5-hydroxy-benzoic acid (3.2 g, 19.6 mmol) in methanol (50 mL). Stir the mixture at 70° C. for 20 hours and then stir at room temperature for 2 days. Evaporate the solvent under reduced pressure and add saturated $NaHCO_3$ water solution (100 mL) into the residue. Filter the precipitated solid and wash it with cold water (20 mL). Dissolve the solid in ethyl acetate (100 mL), dry over $Na_2SO_4$, and concentrate under reduced pressure to give the title compound as a grey solid (2.9 g, 82%): ES/MS (m/z) 178 (M+H), which is used directly without further purification.

Preparation 5

2-Cyano-5-Methylpyridine 1-Oxide

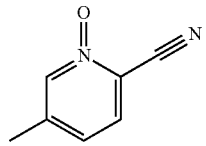

Add m-chloroperoxybenzoic acid (8.0 g, 46 mmol) in batches to a stirred solution of 5-methylpicolinonitrile (4.0 g, 34 mmol) in dichloromethane (60 mL). Stir the mixture under refluxing conditions for 24 hours and cool to room temperature. Wash the mixture with saturated $Na_2S_2O_3$ water solution (3×20 mL) and brine (3×20 mL), dry over $Na_2SO_4$ and concentrate under reduced pressure to give a residue. Purify the residue by silica gel flash chromatography, eluting with a gradient solvent of 50~100% ethyl acetate in petroleum ether to give the title compound as a yellow solid (4.2 g, 92%). ES/MS (m/z) 135 (M+H).

The following compound is prepared essentially by the method of Preparation 5.

TABLE 1

| Prep. No | Chemical Name | Structure | ES/MS (m/z) (M + H) |
|---|---|---|---|
| 6 | 2-Cyano-3-methylpyridine 1-oxide | 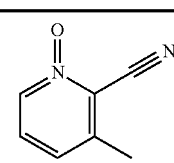 | 135 |

Preparation 7

(6-Cyano-3-methyl-2-pyridyl) acetate

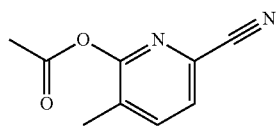

Heat a mixture of 2-cyano-5-methylpyridine 1-oxide (3.7 g, 28 mmol) in acetic acid anhydride (40 mL) at 145° C. with stirring for 64 hours and cool to room temperature. Evaporate the solvent under reduced pressure to give a residue and purify the residue by silica gel flash chromatography, eluting with a gradient solvent of 0~50% ethyl acetate in petroleum ether to give the title compound as a yellow solid (4.0 g, 82%). ES/MS (m/z) 135 (M–$C_2H_3O$+H).

The following compound is prepared essentially by the method of Preparation 7.

TABLE 2

| Prep. No | Chemical Name | Structure | ES/MS (m/z) (M + H) |
|---|---|---|---|
| 8 | (6-Cyano-5-methyl-2-pyridyl) acetate | 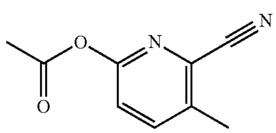 | 135 (M – $C_2H_3O$ + H) |

Preparation 9

6-Hydroxy-5-methyl-pyridine-2-carbonitrile

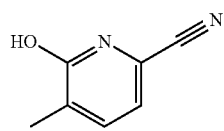

Add sodium hydroxide (2.1 g, 53 mmol) to a stirred solution of (6-cyano-3-methyl-2-pyridyl) acetate (3.4 g, 19 mmol) in methanol (100 mL) and water (100 mL). Stir the mixture at room temperature for 2 hours and evaporate the solvent under reduced pressure. Add citric acid (5.6 g, 29 mmol) and partition the resulting mixture between ethyl acetate (150 mL) and water (120 mL). Isolate the organic phase, wash with brine (3×50 mL), dry over $Na_2SO_4$ and concentrate under reduced pressure to give the title compound as a white solid (2.5 g, 97%), which is used directly without further purification. ES/MS (m/z) 135 (M+H).

The following compound is prepared essentially by the method of Preparation 9.

TABLE 3

| Prep. No | Chemical Name | Structure | ES/MS (m/z) (M + H) |
|---|---|---|---|
| 10 | 6-Hydroxy-3-methyl-pyridine-2-carbonitrile | 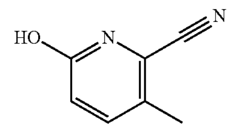 | 135 |

Preparation 11

3-[2-(4-Fluorophenyl)-2-oxo-ethoxy]benzonitrile

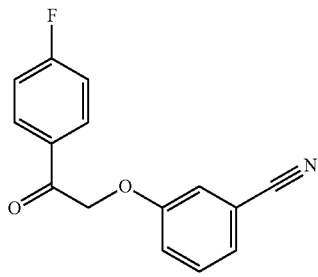 [SMILES: N#Cc1cccc(OCC(=O)c2ccc(F)cc2)c1]

Add potassium carbonate (12.0 g, 86.8 mmol) to a stirred solution of 2-bromo-1-(4-fluorophenyl)ethanone (9.0 g, 41.5 mmol) and 3-hydroxybenzonitrile (5.0 g, 42.0 mmol) in acetonitrile (50 mL). Stir the mixture under refluxing condition for 2 hours. Filter off the solid and concentrate the filtrate under reduced pressure to give the title compound as a white solid (10.8 g, 103% crude), which is used directly without further purification. ES/MS (m/z) 256 (M+H).

The following compound is prepared essentially by the method of Preparation 11.

TABLE 4

| Prep. No | Chemical Name | Structure | ES/MS (m/z) (M + H) |
|---|---|---|---|
| 12 | 3-Fluoro-5-[2-(4-fluorophenyl)-2-oxo-ethoxy]-benzonitrile | 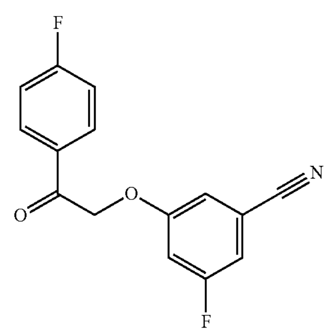 [SMILES: N#Cc1cc(F)cc(OCC(=O)c2ccc(F)cc2)c1] | 274 |

Preparation 13

4-Fluoro-3-[2-(4-fluorophenyl)-2-oxo-ethoxy]benzonitrile

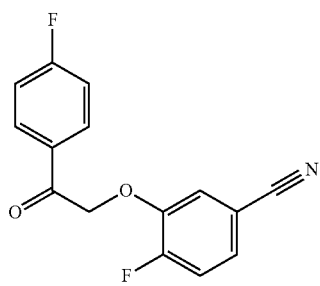 [SMILES: N#Cc1ccc(F)c(OCC(=O)c2ccc(F)cc2)c1]

Add potassium carbonate (1.0 g, 7.5 mmol) to a stirred solution of 2-bromo-1-(4-fluorophenyl)ethanone (1.1 g, 5.0 mmol) and 4-fluoro-3-hydroxybenzonitrile (0.68 g, 5.0 mmol) in acetone (30 mL). Stir the mixture at room temperature for 1 hour. Filter off the solid and concentrate the filtrate under reduced pressure to give a residue. Purify the residue by silica gel flash chromatography, eluting with ethyl acetate:petroleum ether (1:5) to give the title compound as a yellow solid (0.99 g, 73%). ES/MS (m/z) 274 (M+H).

The following compounds are prepared essentially by the method of Preparation 13.

TABLE 5

| Prep. No | Chemical Name | Structure | ES/MS (m/z) (M + H) |
|---|---|---|---|
| 14 | 3-[2-(4-Fluoro-phenyl)-2-oxo-ethoxy]-4-methyl-benzonitrile | | 270 |
| 15 | 3-[2-(4-Fluoro-phenyl)-2-oxo-ethoxy]-4-methoxy-benzonitrile | | 286 |
| 16 | 2-Fluoro-5-[2-(4-fluoro-phenyl)-2-oxo-ethoxy]-benzonitrile | 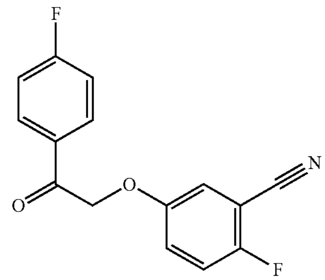 [SMILES: N#Cc1cc(OCC(=O)c2ccc(F)cc2)ccc1F] | 274 |
| 17 | 5-[2-(4-Fluoro-phenyl)-2-oxo-ethoxy]-2-methyl-benzonitrile | 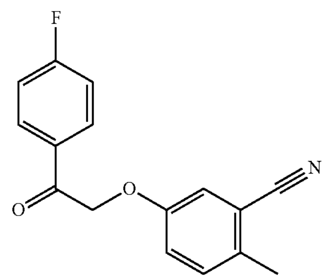 [SMILES: Cc1ccc(OCC(=O)c2ccc(F)cc2)cc1C#N] | 270 |
| 18 | Methyl 3-cyano-5-[2-(4-fluoro-phenyl)-2-oxo-ethoxy]-benzoate | 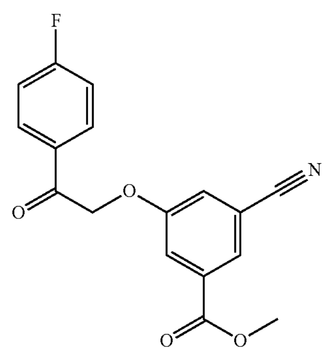 [SMILES: COC(=O)c1cc(C#N)cc(OCC(=O)c2ccc(F)cc2)c1] | 314 |
| 19 | 2-Bromo-5-[2-(4-fluoro-phenyl)-2-oxo-ethoxy]-benzo-nitrile | 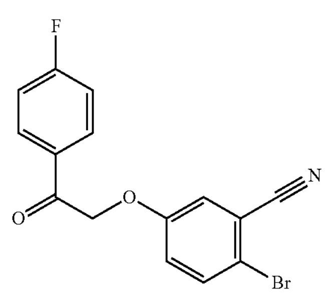 [SMILES: N#Cc1cc(OCC(=O)c2ccc(F)cc2)ccc1Br] | ($^{79}$Br/$^{81}$Br) 333.8/335.8 |

Preparation 20

2-[(6-Bromo-2-pyridyl)oxy]-1-(4-fluorophenyl)ethanone

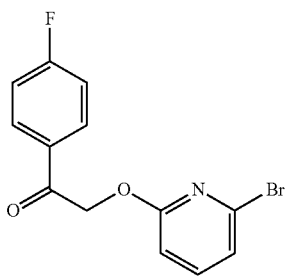 [SMILES: O=C(COc1cc(Br)ccn1)c1ccc(F)cc1]

Add silver(I) carbonate (1.7 g, 6.2 mmol) to a stirred solution of 2-bromo-1-(4-fluorophenyl)ethanone (0.87 g, 4.0 mmol) and 6-bromopyridin-2-ol (0.70 g, 4.0 mmol) in toluene (10 mL). Heat the mixture to 105° C. under microwave irradiation with stirring for 12 hours. Filter off the solid and concentrate the filtrate under reduced pressure to give a residue. Purify the residue by silica gel flash chromatography, eluting with ethyl acetate:hexanes (1:1) to give the title compound as a light yellow solid (0.74 g, 60%). ES/MS (m/z) ($^{79}$Br/$^{81}$Br): 309.9/312.0 [M+H].

The following compound is prepared essentially by the method of Preparation 20.

TABLE 6

| Prep. No | Chemical Name | Structure | ES/MS (m/z) (M + H) |
|---|---|---|---|
| 21 | 2-[(4-Bromo-2-pyridyl)-oxy]-1-(4-fluorophenyl)-ethanone | 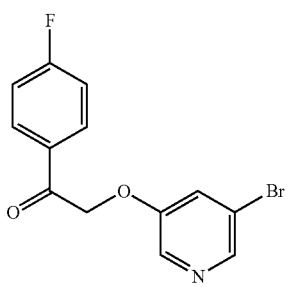 [SMILES: O=C(COc1cncc(Br)c1)c1ccc(F)cc1] | ($^{79}$Br/$^{81}$Br): 309.9/312.0 |

Preparation 22

2-[(5-Bromo-3-pyridyl)oxy]-1-(4-fluorophenyl)ethanone

Add potassium carbonate (8.0 g, 57 mmol) to a stirred solution of 2-bromo-1-(4-fluorophenyl)ethanone (6.2 g, 29 mmol) and 3-bromo-5-hydroxypyridine (5.0 g, 29 mmol) in acetone (100 mL). Stir the mixture at room temperature for 1 hour. Filter off the solid and concentrate the filtrate under reduced pressure to give a residue. Purify the residue by silica gel flash chromatography, eluting with a gradient solvent of 10~30% ethyl acetate in petroleum ether to give the title compound as a yellow solid (3.6 g, 40%). ES/MS (m/z) ($^{79}$Br/$^{81}$Br): 309.8/311.8 [M+H].

The following compound is prepared essentially by the method of Preparation 22.

TABLE 7

| Prep. No | Chemical Name | Structure | ES/MS (m/z) (M + H) |
|---|---|---|---|
| 23 | 2-[(2-Bromo-4-pyridyl)oxy]-1-(4-fluorophenyl)-ethanone | 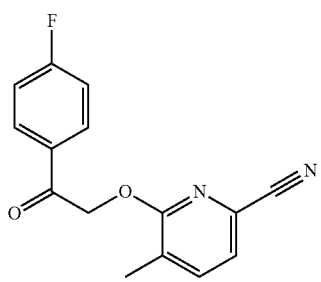 [SMILES: Cc1ccc(C#N)nc1OCC(=O)c1ccc(F)cc1] | ($^{79}$Br/$^{81}$Br): 309.8/311.8 |

Preparation 24

6-[2-(4-Fluorophenyl)-2-oxo-ethoxy]-5-methyl-pyridine-2-carbonitrile

Add potassium carbonate (5.0 g, 36 mmol) to a stirred solution of 2-bromo-1-(4-fluorophenyl)ethanone (3.9 g, 18 mmol) and 6-hydroxy-5-methyl-pyridine-2-carbonitrile (2.4 g, 18 mmol) in acetone (100 mL). Stir the mixture at room temperature for 2 hours and partition between ethyl acetate (150 mL) and water (70 mL). Isolate the organic layer, wash with brine (3×60 mL), dry over Na$_2$SO$_4$ and concentrate under reduced pressure to give a residue. Purify the residue by silica gel flash chromatography, eluting with dichloromethane to give the title compound as a white solid (4.0 g, 79%). ES/MS (m/z) 271 (M+H).

The following compound is prepared essentially by the method of Preparation 24.

TABLE 8

| Prep. No | Chemical Name | Structure | ES/MS (m/z) (M + H) |
|---|---|---|---|
| 25 | 6-[2-(4-Fluorophenyl)-2-oxoethoxy]-3-methylpyridine-2-carbonitrile | 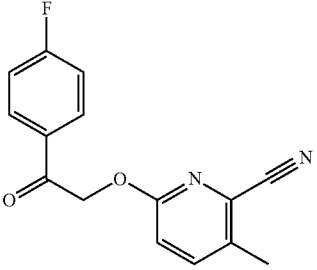 [SMILES: Cc1ccc(OCC(=O)c2ccc(F)cc2)nc1C#N] | 271 |

Preparation 26

(E)-2-[(6-Bromo-2-pyridyl)oxy]-3-(dimethylamino)-1-(4-fluorophenyl)prop-2-en-1-one

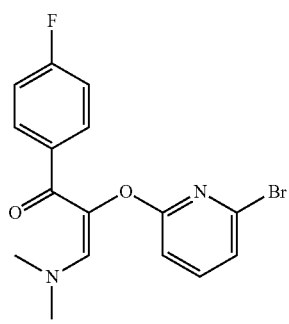 [SMILES: CN(C)/C=C(/Oc1cc(Br)ccn1)C(=O)c1ccc(F)cc1]

Add N,N-dimethylformamide dimethyl acetal (0.30 g, 2.5 mmol) to a stirred solution of 2[(6-bromo-2-pyridyl)oxy]-1-(4-fluorophenyl)ethanone (0.70 g, 2.3 mmol) in toluene (8 mL). Heat the mixture to 120° C. under microwave irradiation with stirring for 3 h and evaporate the solvent under reduced pressure to give a residue. Purify the residue by silica gel flash chromatography, eluting with ethyl acetate:hexanes (1:1) to give the title compound as a yellow solid (0.54 g, 66% yield). ES/MS (m/z) ($^{79}$Br/$^{81}$Br): 365.0/367.0 [M+H].

The following compound is prepared essentially by the method of Preparation 26.

TABLE 9

| Prep. No | Chemical Name | Structure | ES/MS (m/z) (M + H) |
|---|---|---|---|
| 27 | (E)-2-[(4-Bromo-2-pyridyl)oxy]-3-(dimethylamino)-1-(4-fluorophenyl)prop-2-en-1-one | 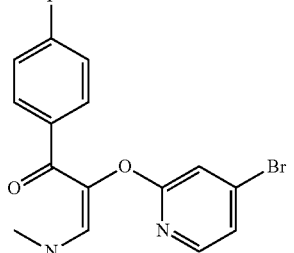 | ($^{79}$Br/$^{81}$Br): 365.0/367.0 |

Preparation 28

(E)-2-[(5-Bromo-3-pyridyl)oxy]-3-(dimethylamino)-1-(4-fluorophenyl)prop-2-en-1-one

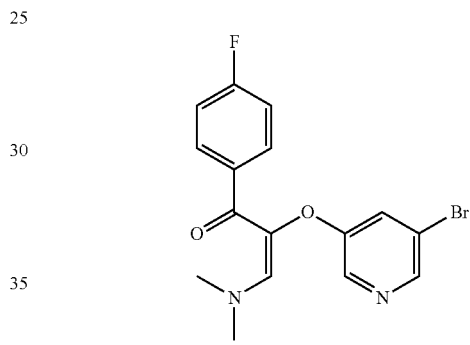

Add N,N-dimethylformamide dimethyl acetal (2.8 g, 23 mmol) to a stirred solution of 2-[(5-bromo-3-pyridyl)oxy]-1-(4-fluorophenyl)ethanone (3.6 g, 12 mmol) in toluene (50 mL). Stir the mixture under refluxing conditions for 18 hours and evaporate the solvent under reduced pressure to give the crude title compound as a yellow gummy solid (4.2 g, 99%), which is used directly without further purification. ES/MS (m/z) ($^{79}$Br/$^{81}$Br): 364.9/366.8 [M+H].

The following compound is prepared essentially by the method of Preparation 28.

TABLE 10

| Prep. No | Chemical Name | Structure | ES/MS (m/z) (M + H) |
|---|---|---|---|
| 29 | (E)-2-[(2-Bromo-4-pyridyl)oxy]-3-(dimethylamino)-1-(4-fluorophenyl)prop-2-en-1-one | 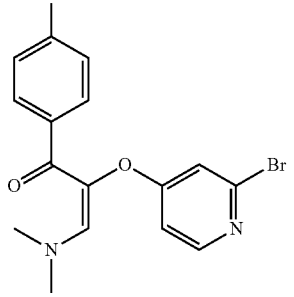 | ($^{79}$Br/$^{81}$Br): 364.9/366.8 |

Preparation 30

6-[(E)-2-(Dimethylamino)-1-(4-fluorobenzoyl)vinyloxy]-5-methyl-pyridine-2-carbonitrile

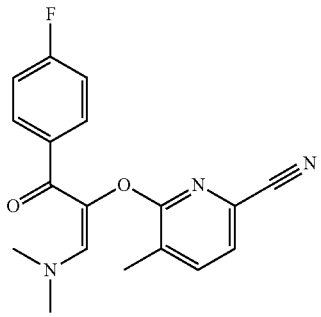 [SMILES: Cc1ccc(C#N)nc1O/C(=C/N(C)C)C(=O)c1ccc(F)cc1]

Add N,N-dimethylformamide dimethyl acetal (4.4 g, 37 mmol) to a stirred solution of 6-[2-(4-fluorophenyl)-2-oxo-ethoxy]-5-methyl-pyridine-2-carbonitrile (1.0 g, 3.7 mmol) in toluene (70 mL). Stir the mixture under refluxing conditions for 40 hours and evaporate the solvent under reduced pressure to give the crude title compound as a brown oil (1.2 g, 100%), which is used directly without further purification. ES/MS (m/z) 326 (M+H).

The following compound is prepared essentially by the method of Preparation 30.

TABLE 11

| Prep. No | Chemical Name | Structure | ES/MS (m/z) (M + H) |
|---|---|---|---|
| 31 | 6-[(E)-2-(Dimethyl-amino)-1-(4-fluoro-benzoyl)-vinyloxy]-3-methyl-pyridine-2-carbonitrile | 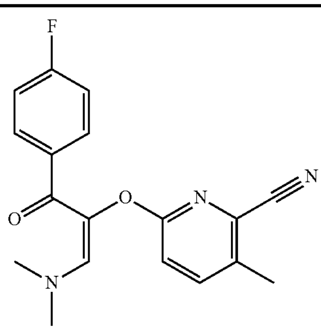 | 326 |

Preparation 32

3-[[3-(4-Fluorophenyl)-1H-pyrazol-4-yl]oxy]benzonitrile

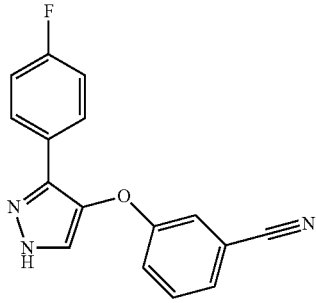 [SMILES: N#Cc1cccc(Oc2c[nH]nc2-c2ccc(F)cc2)c1]

Add N,N-dimethylformamide dimethyl acetal (1.30 g, 10.9 mmol) to a stirred solution of 3-[2-(4-fluorophenyl)-2-oxo-ethoxy]benzonitrile (2.55 g, 10.0 mmol) in toluene (10 mL). Heat the mixture to 120° C. under microwave irradiation with stirring for 1 hour to give 3-[(E)-2-(dimethyl-amino)-1-(4-fluorobenzoyl)vinyloxy]benzonitrile: mass spectrum (m/z): 311(M+H), which is directly used without isolation. Add hydrazine hydrate (0.80 mL, 12.6 mmol) to the reaction and heat the resulting mixture to 120° C. under microwave irradiation with stirring for 3 hours. Evaporate the solvent and purify the residue by silica gel flash chromatography, eluting with ethyl acetate:hexanes (1:1) to give the title compound as a light yellow sticky oil (1.82 g, 65% yield for two steps). ES/MS (m/z) 280 (M+H).

The following compound is prepared essentially by the method of Preparation 32.

TABLE 12

| Prep. No | Chemical Name | Structure | ES/MS (m/z) (M + H) |
|---|---|---|---|
| 33 | 3-Fluoro-5-[2-(4-fluoro-phenyl)-2-oxo-ethoxy]-benzo-nitrile | 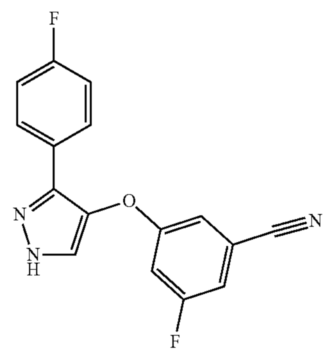 [SMILES: N#Cc1cc(F)cc(Oc2c[nH]nc2-c2ccc(F)cc2)c1] | 298 |

Preparation 34

4-Fluoro-3-[[3-(4-fluorophenyl)-1H-pyrazol-4-yl]oxy]benzonitrile

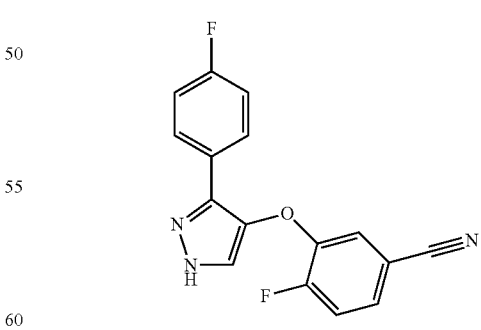

Add N,N-dimethylformamide dimethyl acetal (0.86 g, 7.2 mmol) to a stirred solution of 4-fluoro-3-[2-(4-fluorophenyl)-2-oxo-ethoxy]benzonitrile (0.79 g, 2.9 mmol) in toluene (30 mL). Stir the mixture under refluxing condition for 12 hours and evaporate the solvent under reduced pressure to give a residue. Purify the residue by silica gel flash chromatography, eluting with ethyl acetate:petroleum ether (1:2) to give 3-[(E)-2-(dimethylamino)-1-(4-fluorobenzoyl)vinyloxy]-4-fluoro-benzonitrile (0.72 g, 76% yield): mass spectrum (m/z): 329(M+H). Add hydrazine monohydrochloride (0.26 g, 3.8 mmol) and triethylamine (0.8 mL, 5.7 mmol) to a stirred solution of 3-[(E)-2-(dimethylamino)-1-(4-fluorobenzoyl)vinyloxy]-4-fluoro-benzonitrile (0.63 g, 1.9 mmol) in ethanol (20 mL) and stir the mixture under refluxing condition for 12 hours. Evaporate the solvent and purify the residue by silica gel flash chromatography, eluting with ethyl acetate:petroleum ether (1:2) to give the title compound as a white solid (21 mg, 3.7%). ES/MS (m/z) 298 (M+H).

The following compounds are prepared essentially by the method of Preparation 34.

TABLE 13

| Prep. No | Chemical Name | Structure | ES/MS (m/z) (M + H) |
|---|---|---|---|
| 35 | 2-Bromo-5-[[3-(4-fluoro-phenyl)-1H-pyrazol-4-yl]oxy]-benzonitrile | 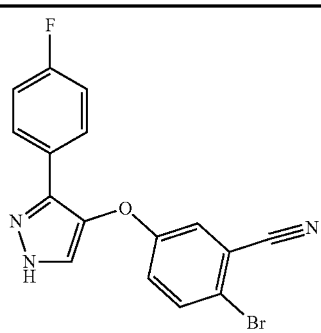 | ($^{79}$Br/$^{81}$Br) 357.9/359.8 |
| 36 | 3-[[3-(4-Fluoro-phenyl)-1H-pyrazol-4-yl]oxy]-4-methyl-benzonitrile | 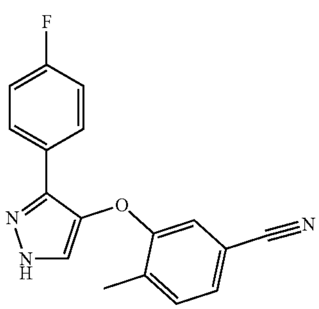 [SMILES: Cc1ccc(C#N)cc1Oc1c[nH]nc1-c1ccc(F)cc1] | 294 |
| 37 | 3-[[3-(4-Fluoro-phenyl)-1H-pyrazol-4-yl]oxy]-4-methoxy-benzonitrile | 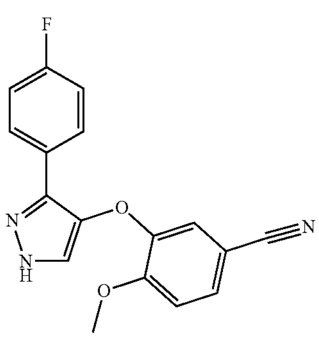 [SMILES: COc1ccc(C#N)cc1Oc1c[nH]nc1-c1ccc(F)cc1] | 310 |
| 38 | 2-Fluoro-5-[[3-(4-fluoro-phenyl)-1H-pyrazol-4-yl]oxy]-benzonitrile | | 298 |
| 39 | 5-[[3-(4-Fluoro-phenyl)-1H-pyrazol-4-yl]oxy]-2-methyl-benzonitrile | | 294 |
| 40 | Methyl 3-cyano-5-[[3-(4-fluoro-phenyl)-1H-pyrazol-4-yl]oxy]-benzoate | | 338 |

Preparation 41

[3-[[3-(4-Fluorophenyl)-1H-pyrazol-4-yl]oxy]phenyl]methanamine

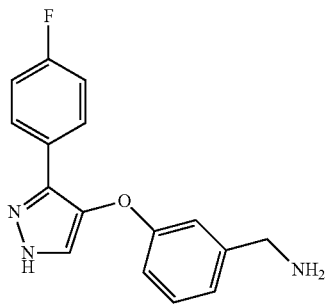 [SMILES: NCc1cccc(Oc2c[nH]nc2-c2ccc(F)cc2)c1]

Add 1 M solution of lithium aluminum hydride in THF (1.2 mL, 1.2 mmol) dropwise to a stirred solution of 3-[[3-(4-fluorophenyl)-1H-pyrazol-4-yl]oxy]benzonitrile (0.28 g, 0.80 mmol) in THF (5 mL) at 0° C. Slowly warm to room temperature and stir for 2 hours. Partition the mixture between ethyl acetate (30 mL) and water (10 mL). Isolate the organic phase, wash with brine, dry over $Na_2SO_4$, and concentrate under reduced pressure to give a residue. Purify the residue by silica gel flash chromatography, eluting with methanol:dicholomethane:ammonium hydroxide (1:9: 0.5) to give the title compound as a white solid (0.12 g, 53%). ES/MS (m/z) 284 (M+H).

Alternate Preparation 41

Add Raney nickel (50 mg, 0.57 mmol) to a stirred solution of 3-[[3-(4-fluorophenyl)-1H-pyrazol-4-yl]oxy]benzonitrile (1.0 g, 3.6 mmol) in 7.0 M ammonium solution in methanol (60 mL). Degas the reaction vessel three times with hydrogen and stir the mixture under hydrogen atmosphere for 20 hours. Filter off the solid and concentrate the filtrate under reduced pressure to give the title compound as a brown oil (1.0 g, 99%), which is used directly without further purification. ES/MS (m/z) 284 (M+H).

The following compounds are prepared essentially by the method of Alternate Preparation 41.

TABLE 14

| Prep. No | Chemical Name | Structure | ES/MS (m/z) (M + H) |
|---|---|---|---|
| 42 | [4-Fluoro-3-[[3-(4-fluorophenyl)-1H-pyrazol-4-yl]oxy]-phenyl]-methanamine | | 302 |
| 43 | [3-[[3-(4-Fluorophenyl)-1H-pyrazol-4-yl]oxy]-4-methyl-phenyl]-methanamine | 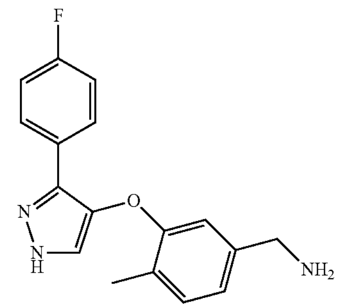 | 298 |
| 44 | [3-[[3-(4-Fluorophenyl)-1H-pyrazol-4-yl]oxy]-4-methoxy-phenyl]-methanamine | 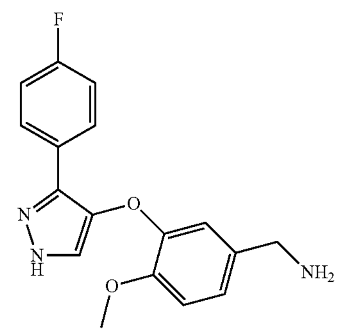 [SMILES: COc1ccc(CN)cc1Oc1c[nH]nc1-c1ccc(F)cc1] | 297 (M − $NH_3$ + H) |
| 45 | [3-Fluoro-5-[[3-(4-fluorophenyl)-1H-pyrazol-4-yl]oxy]-phenyl]-methanamine | 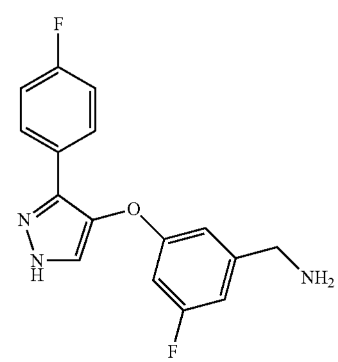 [SMILES: NCc1cc(F)cc(Oc2c[nH]nc2-c2ccc(F)cc2)c1] | 302 |
| 46 | [2-Fluoro-5-[[3-(4-fluorophenyl)-1H-pyrazol-4-yl]oxy]-phenyl]-methanamine | 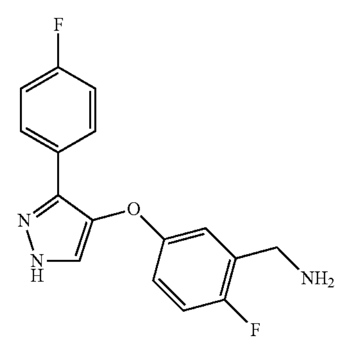 [SMILES: NCc1cc(Oc2c[nH]nc2-c2ccc(F)cc2)ccc1F] | 302 |

TABLE 14-continued

| Prep. No | Chemical Name | Structure | ES/MS (m/z) (M + H) |
|---|---|---|---|
| 47 | [5-[[3-(4-Fluorophenyl)-1H-pyrazol-4-yl]oxy]-2-methylphenyl]methanamine | 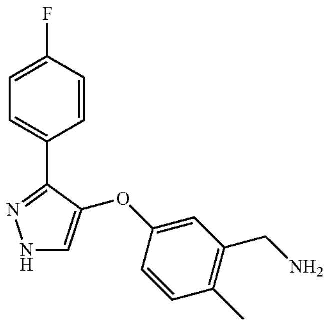 [SMILES: Cc1ccc(Oc2c[nH]nc2-c2ccc(F)cc2)cc1CN] | 298 |
| 48 | Methyl 3-(aminomethyl)-5-[[3-(4-fluorophenyl)-1H-pyrazol-4-yl]oxy]benzoate | 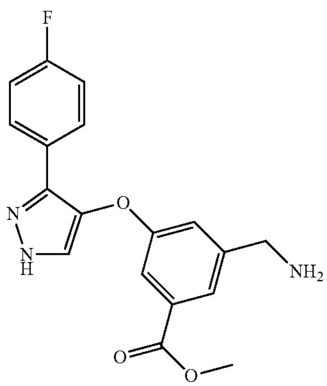 [SMILES: COC(=O)c1cc(CN)cc(Oc2c[nH]nc2-c2ccc(F)cc2)c1] | 342 |

Preparation 49

5-[[3-(4-Fluorophenyl)-1H-pyrazol-4-yl]oxy]-2-(4-methylpiperazin-1-yl)benzonitrile

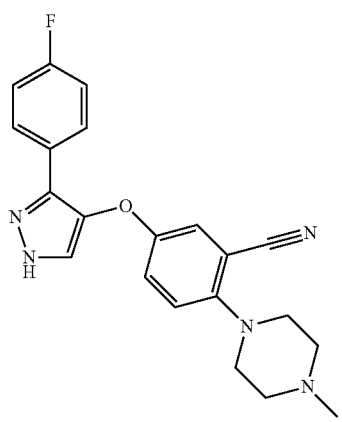 [SMILES: CN1CCN(c2ccc(Oc3c[nH]nc3-c3ccc(F)cc3)cc2C#N)CC1]

Under an $N_2$ atmosphere, stir a mixture of N-methylpiperazine (40 mg, 0.40 mmol), 2-bromo-5-[[3-(4-fluorophenyl)-1H-pyrazol-4-yl]oxy]benzonitrile (120 mg, 0.34 mmol), tris(dibenzylideneacetone)dipalladium(0) (37 mmol, 0.04 mmol), 4,5-bis(diphenylphosphino)-9,9-dimethylxanthene (19 mg, 0.04 mmol), and sodium t-butoxide (64 mg, 0.67 mmol) in 1,4-dioxane (3 mL) at 100° C. for 20 hours. Filter off the solid through a pad of diatomaceous earth and evaporate the solvent under reduced pressure to give a residue. Purify the residue by silica gel flash chromatography, eluting with methanol:dichloromethane (1:10) to give the title compound as a white solid (90 mg, 71%). ES/MS (m/z) 378 (M+H).

Preparation 50

2-Bromo-6-[[3-(4-fluorophenyl)-1H-pyrazol-4-yl]oxy]pyridine

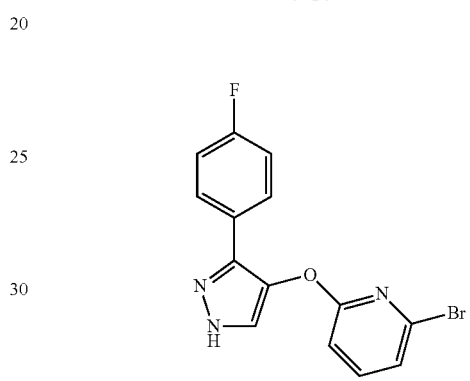

Add hydrazine monohydrochloride (0.11 g, 1.6 mmol) to a stirred solution of (E)-2-[(6-bromo-2-pyridyl)oxy]-3-(dimethylamino)-1-(4-fluorophenyl)prop-2-en-1-one (0.53 g, 1.5 mmol) in ethanol (6 mL). Heat the resulting mixture to 100° C. under microwave irradiation with stirring for 3 hours and evaporate the solvent under reduced pressure to give a residue. Purify the residue by silica gel flash chromatography, eluting with a gradient solvent of 8~25% ethyl acetate in hexanes to give the title compound as a white solid (0.47 g, 97%). ES/MS (m/z) ($^{79}$Br/$^{81}$Br): 334.0/335.9 [M+H].

The following compound is prepared essentially by the method of Preparation 50.

TABLE 15

| Prep. No | Chemical Name | Structure | ES/MS (m/z) (M + H) |
|---|---|---|---|
| 51 | 4-Bromo-2-[[3-(4-fluorophenyl)-1H-pyrazol-4-yl]oxy]pyridine | 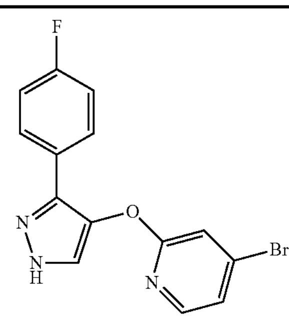 | ($^{79}$Br/$^{81}$Br): 333.9/335.8 |

Preparation 52

3-Bromo-5-[[3-(4-fluorophenyl)-1H-pyrazol-4-yl]oxy]pyridine

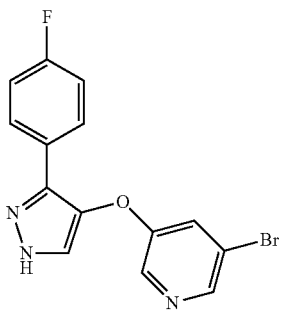 [SMILES: Fc1ccc(-c2n[nH]cc2Oc2cncc(Br)c2)cc1]

Add hydrazine hydrate (2.9 g, 58 mmol) to a stirred solution of (E)-2-[(5-bromo-3-pyridyl)oxy]-3-(dimethylamino)-1-(4-fluorophenyl)prop-2-en-1-one (4.2 g, 12 mmol) in acetic acid (10 mL). Stir the mixture at room temperature for 2 hours and pour into ice water (200 mL). Extract with ethyl acetate (3×50 mL) and wash the combined organic extracts with brine (2×50 mL). Dry over $Na_2SO_4$ and evaporate the solvent under reduced pressure to give a residue. Purify the residue by silica gel flash chromatography, eluting with a gradient solvent of 0~40% ethyl acetate in petroleum ether to give the title compound as a yellow solid (2.4 g, 62%). ES/MS (m/z) ($^{79}$Br/$^{81}$Br): 333.9/335.8 [M+H].

The following compound is prepared essentially by the method of Preparation 52.

TABLE 16

| Prep. No | Chemical Name | Structure | ES/MS (m/z) (M + H) |
|---|---|---|---|
| 53 | 2-Bromo-4-[[3-(4-fluorophenyl)-1H-pyrazol-4-yl]oxy]pyridine | 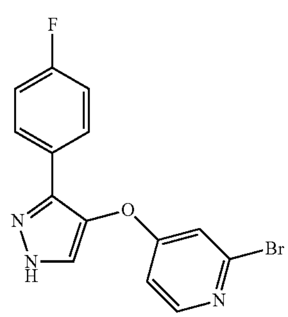 [SMILES: Fc1ccc(-c2n[nH]cc2Oc2ccnc(Br)c2)cc1] | ($^{79}$Br/$^{81}$Br): 333.9/335.8 |

Preparation 54

6-[[3-(4-Fluorophenyl)-1H-pyrazol-4-yl]oxy]pyridine-2-carbonitrile

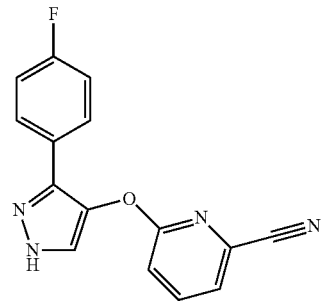

Add zinc cyanide (0.22 g, 1.9 mmol), [1,1'-bis(diphenylphosphino) ferrocene]dichloropalladium(II) (0.11 g, 0.13 mmol), zinc (50 mg, 0.76 mmol) and zinc acetate (0.13 g, 0.71 mmol) to a stirred solution of 2-bromo-6-[[3-(4-fluorophenyl)-1H-pyrazol-4-yl]oxy]pyridine (0.47 g, 1.4 mmol) in dimethylacetamide (8 mL). Heat the resulting mixture to 160° C. under microwave irradiation with stirring for 2.5 hours. Filter off the solid and partition the filtrate between diethyl ether (50 mL) and water (20 mL). Isolate the organic phase and extract the aqueous phase with diethyl ether (2×20 mL). Combine all the organic extracts, wash with brine, dry over $Na_2SO_4$ and concentrate under reduced pressure to give a residue. Purify the residue by silica gel flash chromatography, eluting with a gradient solvent of 7~35% ethyl acetate in hexanes to give the title compound as a white solid (54 mg, 14%). ES/MS (m/z) 281 (M+H).

The following compound is prepared essentially by the method of Preparation 54.

TABLE 17

| Prep. No | Chemical Name | Structure | ES/MS (m/z) (M + H) |
|---|---|---|---|
| 55 | 2-[[3-(4-Fluorophenyl)-1H-pyrazol-4-yl]oxy]-pyridine-4-carbonitrile | 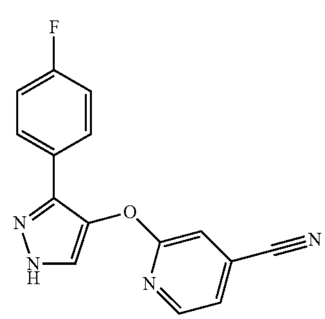 [SMILES: N#Cc1ccnc(Oc2c[nH]nc2-c2ccc(F)cc2)c1] | 281 |

Preparation 56

5-[[3-(4-Fluorophenyl)-1H-pyrazol-4-yl]oxy]pyridine-3-carbonitrile

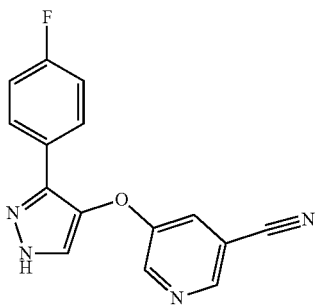 [SMILES: N#Cc1cncc(Oc2c[nH]nc2-c2ccc(F)cc2)c1]

Add copper cyanide (0.92 g, 10 mmol) to a stirred solution of 3-bromo-5-[[3-(4-fluorophenyl)-1H-pyrazol-4-yl]oxy]pyridine (2.3 g, 6.9 mmol) in N-methylpyrrolidone (1 mL). Purge the reaction vessel with nitrogen and heat the mixture to 200° C. under microwave irradiation with stirring for 30 minutes. Pour the mixture into a stirred solution of ethylenediamine (40 mL) in water (160 mL) and stir for 15 min. Extract the mixture with ethyl acetate (3×100 mL) and combine all the organic phases. Wash with brine (2×100 mL), dry over $Na_2SO_4$ and concentrate under reduced pressure to give a residue. Purify the residue by silica gel flash chromatography, eluting with a gradient solvent of 0~50% ethyl acetate in petroleum ether to give the title compound as a yellow solid (1.7 g, 86%). ES/MS (m/z) 281 (M+H).

The following compound is prepared essentially by the method of Preparation 56.

TABLE 18

| Prep. No | Chemical Name | Structure | ES/MS (m/z) (M + H) |
|---|---|---|---|
| 57 | 4-[[3-(4-Fluorophenyl)-1H-pyrazol-4-yl]oxy]-pyridine-2-carbonitrile | 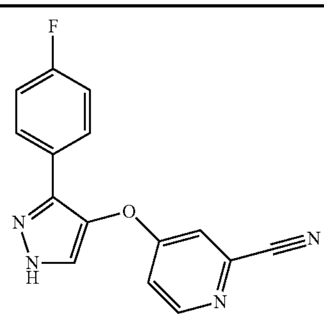 | 281 |

Preparation 58

6-[[3-(4-Fluorophenyl)-1H-pyrazol-4-yl]oxy]-5-methyl-pyridine-2-carbonitrile

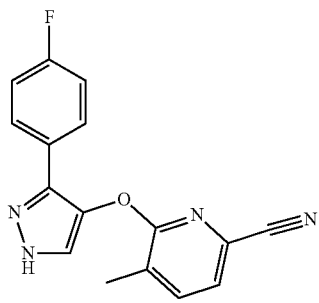 [SMILES: Cc1ccc(C#N)nc1Oc1c[nH]nc1-c1ccc(F)cc1]

Add hydrazine hydrate (0.74 g, 15 mmol) to a stirred solution of 6-[(E)-2-(dimethylamino)-1-(4-fluorobenzoyl)vinyloxy]-5-methyl-pyridine-2-carbonitrile (1.2 g, 3.7 mmol) in acetic acid (10 mL). Stir the mixture at room temperature for 1 hour and pour into ice water (100 mL). Collect the precipitate by filtration and wash with cold water (3×10 mL). Dissolve the solid in ethyl acetate (50 mL), dry over $Na_2SO_4$ and evaporate the solvent under reduced pressure to give the crude title compound as a yellow solid (0.80 g, 74%), which is used directly without further purification. ES/MS (m/z) 295 (M+H).

The following compounds are prepared essentially by the method of Preparation 58.

TABLE 19

| Prep. No | Chemical Name | Structure | ES/MS (m/z) (M + H) |
|---|---|---|---|
| 59 | 6-[[3-(4-Fluorophenyl)-1H-pyrazol-4-yl]oxy]-3-methyl-pyridine-2-carbonitrile | 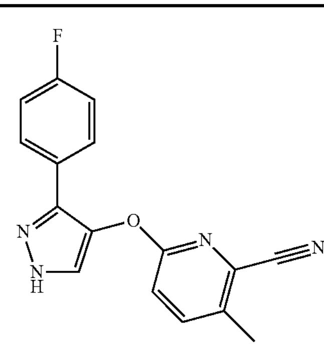 | 295 |

Preparation 60

[6-[[3-(4-Fluorophenyl)-1H-pyrazol-4-yl]oxy]-2-pyridyl]methanamine

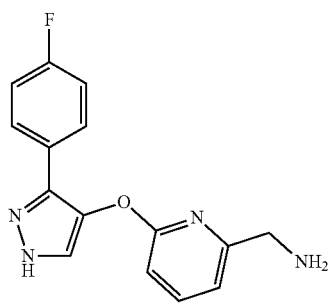 [SMILES: NCc1cccc(Oc2c[nH]nc2-c2ccc(F)cc2)n1]

Add Raney nickel (0.3 mL, 3.5 mmol) to a stirred solution of 6-[[3-(4-fluorophenyl)-1H-pyrazol-4-yl]oxy]pyridine-2-carbonitrile (50 mg, 0.18 mmol) in 7.0 M ammonium solution in methanol (7 mL). Degas the reaction vessel three times with hydrogen and stir the mixture under a hydrogen atmosphere for 18 hours. Filter off the solid through a pad of diatomaceous earth and concentrate the filtrate under reduced pressure to give the title compound as a brown oil (50 mg, 100%), which is used directly without further purification. ES/MS (m/z) 285 (M+H).

The following compounds are prepared essentially by the method of Preparation 60.

TABLE 20

| Prep. No | Chemical Name | Structure | ES/MS (m/z) (M + H) |
|---|---|---|---|
| 61 | [2-[[3-(4-Fluorophenyl)-1H-pyrazol-4-yl]oxy]-4-pyridyl]methanamine | 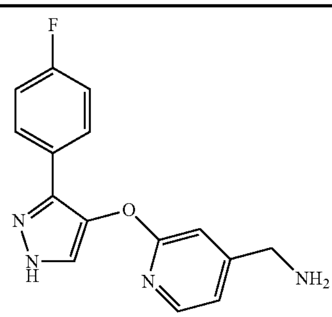 | 285 |
| 62 | [5-[[3-(4-Fluorophenyl)-1H-pyrazol-4-yl]oxy]-3-pyridyl]methanamine | 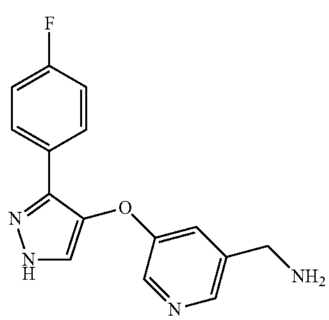 [SMILES: NCc1cncc(Oc2c[nH]nc2-c2ccc(F)cc2)c1] | 285 |
| 63 | [4-[[3-(4-Fluorophenyl)-1H-pyrazol-4-yl]oxy]-2-pyridyl]methanamine | 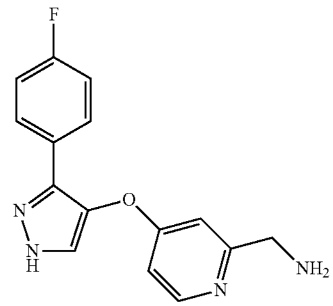 [SMILES: NCc1cc(Oc2c[nH]nc2-c2ccc(F)cc2)ccn1] | 285 |
| 64 | [6-[[3-(4-Fluorophenyl)-1H-pyrazol-4-yl]oxy]-5-methyl-2-pyridyl]methanamine | 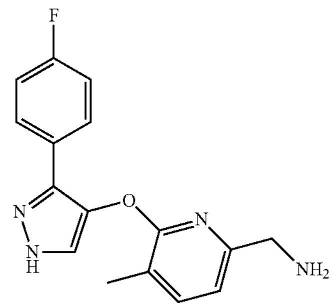 [SMILES: Cc1ccc(CN)nc1Oc1c[nH]nc1-c1ccc(F)cc1] | 299 |
| 65 | [6-[[3-(4-Fluorophenyl)-1H-pyrazol-4-yl]oxy]-3-methyl-2-pyridyl]methanamine | 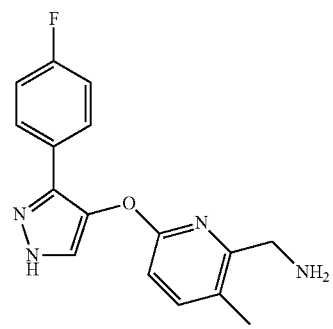 | 299 |

Preparation 66

Methyl 3-[[3-(4-fluorophenyl)-1H-pyrazol-4-yl]oxy]-5-(ureidomethyl)benzoate

Methyl 3-[[3-(4-fluorophenyl)-1H-pyrazol-4-yl]oxy]-5-(ureidomethyl)benzoate is prepared substantially as described by Example 1 to give the title compound as a white solid. ES/MS (m/z) 341 (M+H).

Example 1

[3-[[3-(4-Fluorophenyl)-1H-pyrazol-4-yl]oxy]phenyl]methylurea

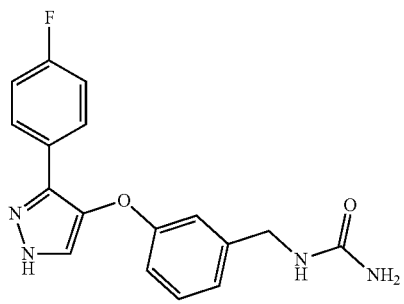 [SMILES: NC(=O)NCc1cccc(Oc2c[nH]nc2-c2ccc(F)cc2)c1]

Add phenylurethane (70 mg, 0.51 mmol) to a stirred solution of [3-[[3-(4-fluorophenyl)-1H-pyrazol-4-yl]oxy] phenyl]methanamine (0.12 g, 0.42 mmol) in THF (5 mL) and then add diisopropylethylamine (0.16 mL, 0.92 mmol). Heat the resulting mixture to 80° C. under microwave irradiation with stirring for 6 hours. Partition between ethyl acetate (30 mL) and water (10 mL). Isolate the organic phase, wash with brine, dry over $Na_2SO_4$ and concentrate under reduced pressure to give a residue. Purify the residue by silica gel flash chromatography, eluting with methanol:dicholomethane (1:9) to give the title compound as a white solid (0.12 g, 87%). ES/MS (m/z) 327 (M+H).

Alternate Example 1

Add potassium cyanate (0.22 g, 2.7 mmol) to a stirred solution of [3-[[3-(4-fluorophenyl)-1H-pyrazol-4-yl]oxy] phenyl]methanamine (0.75 g, 2.5 mmol) in a mixture of methanol (5 mL) and acetic acid (0.1 mL). Heat the resulting mixture to 80° C. under microwave irradiation with stirring for 1 hour. Evaporate the solvent under reduced pressure and purify the residue by silica gel flash chromatography, eluting with methanol:dicholomethane (1:9) to give the title compound as a white solid (0.68 g, 83%). ES/MS (m/z) 327 (M+H).

The following compounds are prepared essentially by the method of Alternate Example 1.

TABLE 21

| Ex. No | Chemical Name | Structure | ES/MS (m/z) (M + H) |
|---|---|---|---|
| 2 | [4-Fluoro-3-[[3-(4-fluorophenyl)-1H-pyrazol-4-yl]oxy]phenyl]-methylurea | 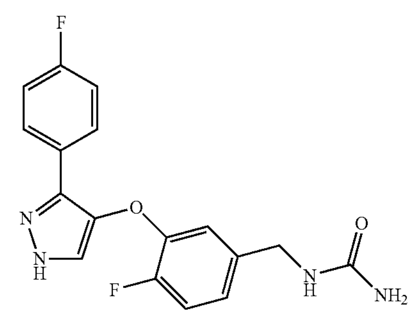 | 345 |
| 3 | [3-[[3-(4-Fluorophenyl)-1H-pyrazol-4-yl]oxy]-4-methylphenyl]-methylurea | 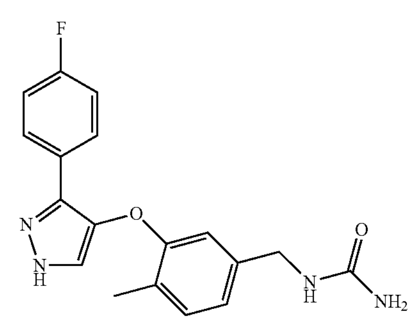 [SMILES: Cc1ccc(CNC(N)=O)cc1Oc1c[nH]nc1-c1ccc(F)cc1] | 341 |

TABLE 21-continued

| Ex. No | Chemical Name | Structure | ES/MS (m/z) (M + H) |
|---|---|---|---|
| 4 | [3-[[3-(4-Fluorophenyl)-1H-pyrazol-4-yl]oxy]-4-methoxyphenyl]methylurea | 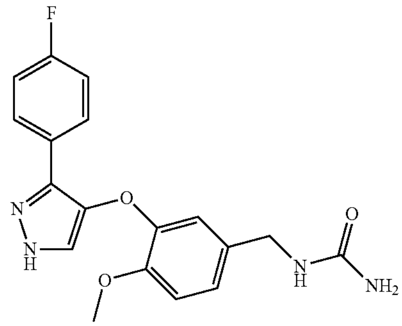 [SMILES: COc1ccc(CNC(N)=O)cc1Oc1c[nH]nc1-c1ccc(F)cc1] | 357 |
| 5 | [3-Fluoro-5-[[3-(4-fluorophenyl)-1H-pyrazol-4-yl]oxy]phenyl]methylurea | 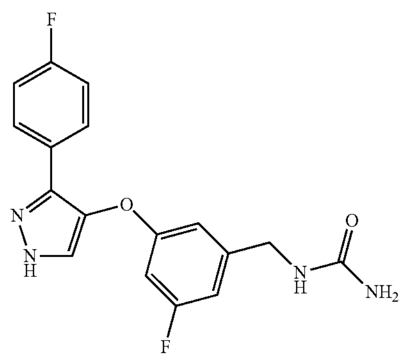 [SMILES: NC(=O)NCc1cc(F)cc(Oc2c[nH]nc2-c2ccc(F)cc2)c1] | 345 |
| 6 | [2-Fluoro-5-[[3-(4-fluorophenyl)-1H-pyrazol-4-yl]oxy]phenyl]methylurea | 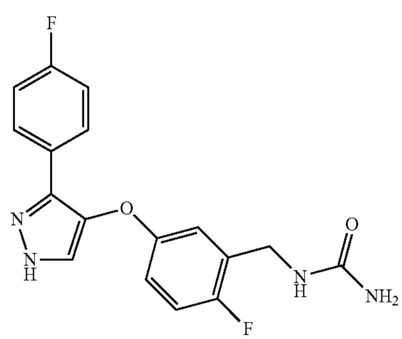 [SMILES: NC(=O)NCc1cc(Oc2c[nH]nc2-c2ccc(F)cc2)ccc1F] | 345 |

TABLE 21-continued

| Ex. No | Chemical Name | Structure | ES/MS (m/z) (M + H) |
|---|---|---|---|
| 7 | [5-[[3-(4-Fluorophenyl)-1H-pyrazol-4-yl]oxy]-2-methylphenyl]-methylurea | 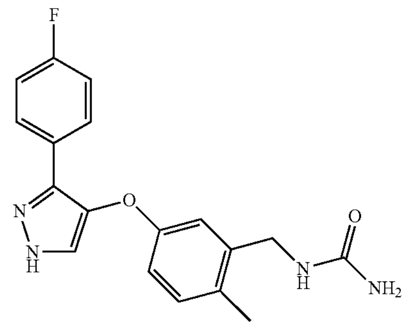 | 341 |
| 8 | [5-[[3-(4-Fluorophenyl)-1H-pyrazol-4-yl]oxy]-2-(4-methylpiperazin-1-yl)phenyl]methylurea | 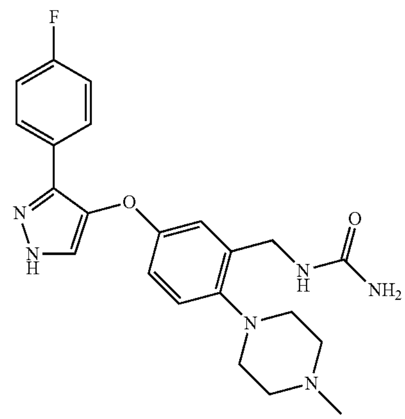 [SMILES: CN1CCN(c2ccc(Oc3c[nH]nc3-c3ccc(F)cc3)cc2CNC(N)=O)CC1] | 425 |

Example 9

3-[[3-(4-Fluorophenyl)-1H-pyrazol-4-yl]oxy]-5-(ureidomethyl)benzoic acid

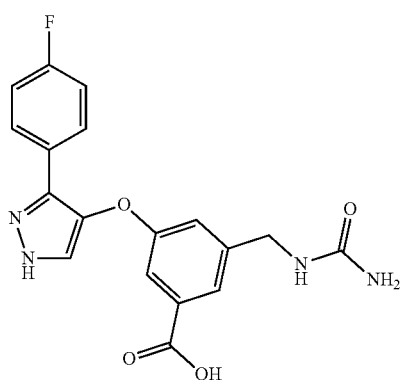 [SMILES: NC(=O)NCc1cc(Oc2c[nH]nc2-c2ccc(F)cc2)cc(C(=O)O)c1]

Add lithium hydroxide (0.18 g, 4.4 mmol) to a stirred solution of methyl 3-[[3-(4-fluorophenyl)-1H-pyrazol-4-yl]oxy]-5-(ureidomethyl)benzoate (0.15 g, 0.44 mmol) in methanol (15 mL) and water (4 mL). Stir the mixture at room temperature for 20 hours and evaporate the solvent under reduced pressure to give a residue. Purify the residue by reverse phase flash chromatography, eluting with acetonitrile and 0.05% $NH_4HCO_3$ in water in a gradient 0~35% to give the title compound as a white solid (95 mg, 58%). ES/MS (m/z 371 (M+H).

Example 10

3-[[3-(4-Fluorophenyl)-1H-pyrazol-4-yl]oxy]-5-(ureidomethyl)benzamide

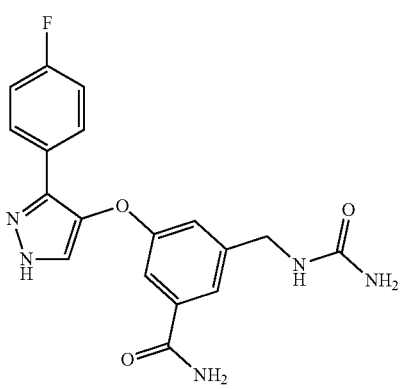 [SMILES: NC(=O)NCc1cc(Oc2c[nH]nc2-c2ccc(F)cc2)cc(C(N)=O)c1]

Add 1-[bis(dimethylamino)methylene]-1H-1,2,3-triazolo[4,5-b]pyridinium 3-oxid hexafluorophosphate (67 mg, 0.18 mmol) and diisopropylethylamine (0.12 mL, 0.68 mmol) to a stirred solution of 3-[[3-(4-fluorophenyl)-1H-pyrazol-4-yl]oxy]-5-(ureidomethyl)benzoic acid (50 mg, 0.14 mmol) and ammonium chloride (36 mg, 0.68 mmol) in DMF (1 mL). Stir the mixture at room temperature for 2 hours. Purify the mixture by reverse phase flash chromatography, eluting with acetonitrile and 0.05% $NH_4HCO_3$ in water in a gradient 0~35% to give the title compound as a white solid (35 mg, 70%). ES/MS (m/z) 370 (M+H).

Example 11

[6-[[3-(4-Fluorophenyl)-1H-pyrazol-4-yl]oxy]-2-pyridyl]methylurea

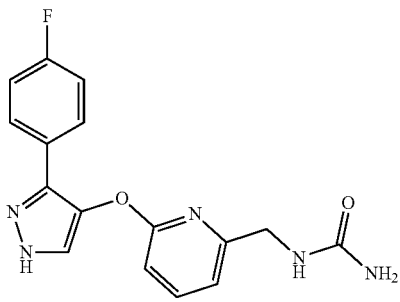 [SMILES: NC(=O)NCc1cccc(Oc2c[nH]nc2-c2ccc(F)cc2)n1]

Add potassium cyanate (16 mg, 0.20 mmol) to a stirred solution of [6-[[3-(4-fluorophenyl)-1H-pyrazol-4-yl]oxy]-2-pyridyl]methanamine (50 mg, 0.17 mmol) in a mixture of methanol (5 mL) and acetic acid (0.1 mL). Heat the resulting mixture to 80° C. under microwave irradiation with stirring for 1 hour. Evaporate the solvent under reduced pressure and purify the residue by silica gel flash chromatography, eluting with a gradient solvent of 0~10% methanol in dicholomethane to give the title compound as a white solid (30 mg, 55%). ES/MS (m/z) 328 (M+H).

The following compounds are prepared essentially by the method of Example 11.

TABLE 22

| Ex. No | Chemical Name | Structure | ES/MS (m/z) (M + H) |
|---|---|---|---|
| 12 | [2-[[3-(4-Fluorophenyl)-1H-pyrazol-4-yl]oxy]-4-pyridyl]methylurea | 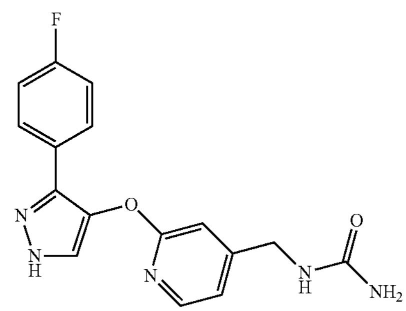 [SMILES: NC(=O)NCc1ccnc(Oc2c[nH]nc2-c2ccc(F)cc2)c1] | 328 |
| 13 | 5-[[3-(4-Fluorophenyl)-1H-pyrazol-4-yl]oxy]-3-pyridyl]methylurea | 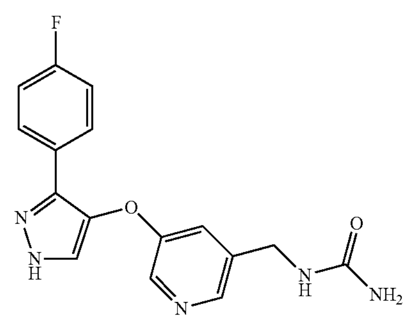 [SMILES: NC(=O)NCc1cncc(Oc2c[nH]nc2-c2ccc(F)cc2)c1] | 328 |
| 14 | [4-[[3-(4-fluorophenyl)-1H-pyrazol-4-yl]oxy]-2-pyridyl]methylurea | 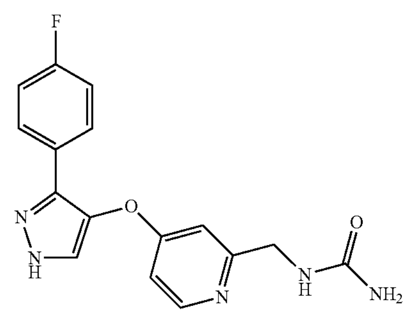 [SMILES: NC(=O)NCc1cc(Oc2c[nH]nc2-c2ccc(F)cc2)ccn1] | 328 |

TABLE 22-continued

| Ex. No | Chemical Name | Structure | ES/MS (m/z) (M + H) |
|---|---|---|---|
| 15 | [6-[[3-(4-Fluorophenyl)-1H-pyrazol-4-yl]oxy]-5-methyl-2-pyridyl]methylurea | 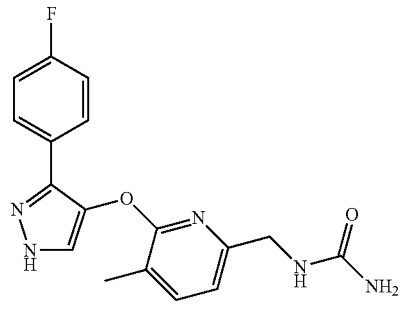 [SMILES: Cc1ccc(CNC(N)=O)nc1Oc1c[nH]nc1-c1ccc(F)cc1] | 342 |
| 16 | [6-[[3-(4-Fluorophenyl)-1H-pyrazol-4-yl]oxy]-3-methyl-2-pyridyl]methylurea | 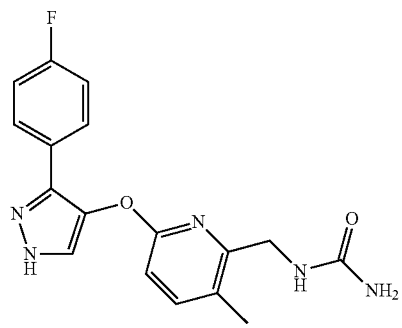 [SMILES: Cc1ccc(Oc2c[nH]nc2-c2ccc(F)cc2)nc1CNC(N)=O] | 342 |

Assays

Enzymatic Activity Assay of MetAP2 and MetAP1

The compounds exemplified herein are tested essentially as described below and exhibit an $IC_{50}$ for the human and mouse MetAP2 assay of lower than 500 nM and are considered selective for MetAP2 with a MetAP1 value greater than 30 µM.

Full length MetAP2 (human and mouse) and MetAP1 (human) proteins are generated from Sf9 cells using procedure similar to that described in Biochemistry 2003, 42, 5035-5042. MetAP2 and MetAP1 are purified in the presence of 5 mM $MnCl_2$ and 2 mM $CoCl_2$ respectively, and stored at −78° C. before use.

Compound inhibition of the catalytic activity of human and mouse MetAP2 in the present invention is monitored by the formation of the product peptide (Gly-Lys-Val-Lys-Val-Gly-Val-Asn-Gly) from the substrate peptide (Met-Gly-Lys-Val-Lys-Val-Gly-Val-Asn-Gly) via LC/MS detection. The reaction is typically conducted by incubating the enzyme, testing compound and substrate (150 µM) in a 100 µl assay buffer (50 mM HEPES, 100 mM NaCl, 50 mg/mL BSA, 0.17 mM Triton X-100 at pH 7.5) for 40 min. After the reaction is stopped by the addition of 200 µl acetonitrile, the levels of product and remaining substrate are quantified on a mass spectrometer. The activity of human MetAP1 is monitored by the formation of the fluorescent product rhodmine-methionine from the substrate methionine-rhodamine-methionine on a spectrophotometer with the excitation light at 460 nm and emission light at 535 nm. The reaction is typically conducted by incubating the enzyme, testing compound and substrate (50 µM) in a 100 µl assay buffer (50 mM HEPES, 100 mM NaCl, 0.1% BSA, 0.05% Tween-20, 50 µM $CoCl_2$) for 60 min. $IC_{50}$ value (concentrations of testing compound that provides a 50% inhibition of MetAP2 activity) are calculated typically from a 10-point dose titration curve using the 4-parameter equation. For Example 1, the $IC_{50}$ value for hMetAP2 is 11 nM and mMetAP2 is 36 nM. Example 1 has an $IC_{50}$>30 µM for MetAP1, demonstrating selective MetAP2 inhibition as compared with MetAP1. The $IC_{50}$ for the human and mouse MetAP2 assay using exemplified compounds is lower than 500 nM and IC50 value for hMetAP1 is >30 µM, demonstrating selective MetAP2 inhibition as compared with MetAP1.

Therapeutic Weight Loss Effect Measurement of Compounds

To determine the therapeutic weight loss effects and improvement of metabolic parameters, compounds from the invention are tested in the high fat diet (HFD) feeding induced obese mouse model (DIO mice). In this model, C57/B16J male mouse is fed with the 60% HFD (D12492i, Research Diets) for 16~28 weeks to establish obesity with body weight reaching around 50 g. The mice will gradually increase the body weight to about 50 g and maintain that weight in this obese state. Test compound (via the vehicle of 0.5% HEC plus 0.25% Tween-80 at 5 mL/kg) is administered orally to the obese DIO mice once or twice daily throughout the study duration. The dose-dependent weight loss of obese DIO mice for Example 1 of the oral treatment at 30 mg/kg twice a day is about 6%, 10%, and 14% weight loss compared to the vehicle group at day 7, day 14, and day 21 respectively. The data support that the compound of Example 1 is associated with desired weight loss and offers therapeutic weight loss effect.

The exemplified compounds of the present invention can be readily formulated into pharmaceutical compositions in accordance with accepted practices known in the art such as found in Remington's "Pharmaceutical Sciences", Gennaro, Ed., Mack Publishing Co. Easton Pa. 1990 such as tablets, solid or gel filled capsules, powders, suspensions, or solutions. The composition can also include one or more pharmaceutically acceptable carriers, excipients, and diluents.

Preferred pharmaceutical compositions are formulated as a tablet or capsule for oral administration. The tablet or capsule can include a compound of the present invention in an amount effective to treat obesity.

The pharmaceutical composition is administered to a patient in amounts effective to treat obesity. An appropriate amount or dose effective to treat a patient can be determined by a health care provider.

What is claimed is:

1. A compound which is

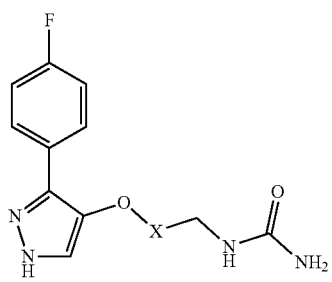

wherein X is selected from the group consisting of

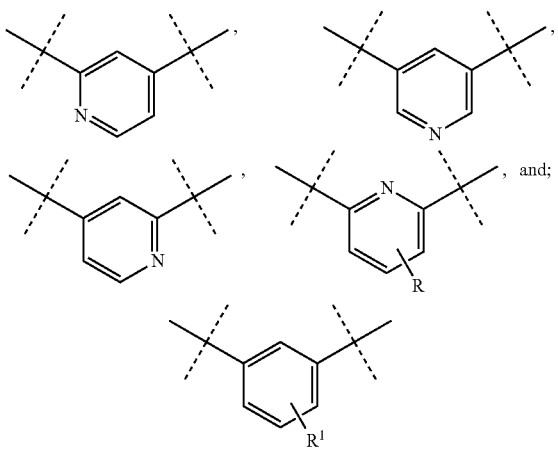

R is selected from the group consisting of H and CH₃;

R¹ is selected from the group consisting of H, CH₃, F, Cl, OCH₃, C(O)OH, C(O)NH₂ and

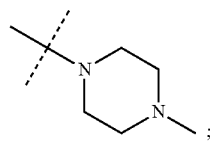

or a pharmaceutically acceptable salt thereof.

2. A compound or pharmaceutically acceptable salt thereof, as claimed by claim 1 wherein X is

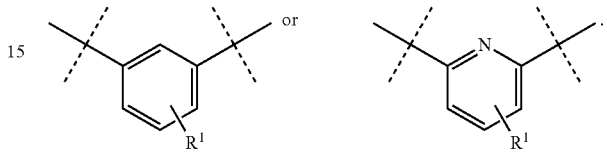

3. A compound or pharmaceutically acceptable salt thereof, as claimed by claim 1 wherein X is

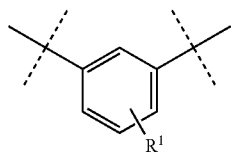

4. A compound or salt as claimed by claim 3 wherein R¹ is selected from the group consisting of H, F, and CH₃.

5. A compound or salt as claimed by claim 3 wherein R¹ is

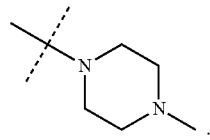

6. A compound as claimed by claim 1 wherein the compound is [3-[[3-(4-Fluorophenyl)-1H-pyrazol-4-yl]oxy]phenyl]methylurea, or a pharmaceutically acceptable salt thereof.

7. A compound or salt as claimed by claim 1 wherein X is

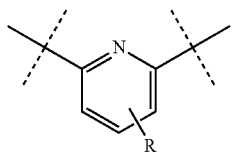

8. A compound or salt as claimed by claim 7 wherein R is CH₃.

9. A compound as claimed by claim 1 wherein the compound is [6-[[3-(4-Fluorophenyl)-1H-pyrazol-4-yl]oxy]-5-methyl-2-pyridyl]methylurea or a pharmaceutically acceptable salt thereof.

10. A method of providing desired weight loss in a mammal in need thereof, comprising administering an effective amount of a compound as claimed by claim 1, or a pharmaceutically acceptable salt thereof.

11. A method of treating obesity in a mammal in need thereof, comprising administering an effective amount of a compound as claimed by claim 1, or a pharmaceutically acceptable salt thereof.

12. A method for providing therapeutic weight loss in a mammal in need thereof, comprising administering an effective amount of a compound as claimed by claim 1, or a pharmaceutically acceptable salt thereof.

13. A pharmaceutical composition comprising a compound as claimed by claim 1 or a pharmaceutically acceptable salt thereof, and at least one pharmaceutically acceptable carrier, diluent, or excipient.

* * * * *